(12) United States Patent
Astle

(10) Patent No.: US 6,878,345 B1
(45) Date of Patent: Apr. 12, 2005

(54) ULTRA HIGH THROUGHPUT BIOASSAY SCREENING SYSTEM

(76) Inventor: Thomas W. Astle, 607 Harborview Rd., Orange, CT (US) 06477

(*) Notice: Subject to any disclaimer, the term of this patent is extended or adjusted under 35 U.S.C. 154(b) by 0 days.

(21) Appl. No.: 09/198,018

(22) Filed: Nov. 23, 1998

Related U.S. Application Data

(60) Provisional application No. 60/095,497, filed on Aug. 6, 1998, provisional application No. 60/073,329, filed on Feb. 2, 1998, and provisional application No. 60/067,895, filed on Dec. 8, 1997.

(51) Int. Cl.$^7$ ................................................. B01L 3/00
(52) U.S. Cl. ..................... 422/102; 422/66; 422/99; 436/44; 435/288.3; 435/288.4; 53/411; 53/412; 53/420
(58) Field of Search ..................... 422/63, 66, 68.1, 422/82.05; 436/43, 44, 47, 48; 435/286.2, 287.1, 287.2, 287.5, 288.3, 288.4, 288.7; 53/412, 415, 420, 453

(56) References Cited

U.S. PATENT DOCUMENTS

| | | | | |
|---|---|---|---|---|
| 3,526,480 A | * | 9/1970 | Findl et al. | 356/38 |
| 3,620,678 A | * | 11/1971 | Guigan | 23/253 R |
| 4,159,953 A | * | 7/1979 | Paquette | 210/396 |
| 4,263,256 A | * | 4/1981 | Morle | 356/246 |
| 4,264,560 A | * | 4/1981 | Natelson | 422/58 |
| 4,508,686 A | * | 4/1985 | Shaber et al. | 422/55 |
| 4,565,783 A | * | 1/1986 | Hansen et al. | 435/299 |
| 4,714,595 A | * | 12/1987 | Anthony et al. | 422/294 |
| 4,853,059 A | * | 8/1989 | Meguro et al. | 156/157 |
| 4,863,693 A | * | 9/1989 | Howell | 356/246 |
| 4,878,971 A | * | 11/1989 | Tsunekawa et al. | 156/70 |
| 4,883,642 A | * | 11/1989 | Bisconte | 422/102 |
| 4,952,266 A | * | 8/1990 | Tsuruta et al. | 156/243 |
| 4,978,505 A | * | 12/1990 | Kertz | 422/63 |
| 5,092,466 A | * | 3/1992 | Anderson | 206/438 |
| 5,213,766 A | * | 5/1993 | Flesher et al. | 422/102 |
| 5,418,022 A | * | 5/1995 | Anderson et al. | 428/35.2 |
| 5,447,679 A | * | 9/1995 | Eigen et al. | 264/544 |
| 5,526,935 A | * | 6/1996 | Tidemann et al. | 206/713 |
| 5,582,665 A | * | 12/1996 | Eigen et al. | 156/69 |
| 5,789,251 A | * | 8/1998 | Astle | 436/48 |
| 5,979,653 A | * | 11/1999 | Owens et al. | 206/484.1 |
| 5,983,607 A | * | 11/1999 | Mihalov et al. | 53/478 |

* cited by examiner

*Primary Examiner*—Jill Warden
*Assistant Examiner*—Dwayne K Handy
(74) *Attorney, Agent, or Firm*—John H. Crozier

(57) ABSTRACT

In a preferred embodiment, a method of performing biological assays, including: providing a longitudinally extending carrier tape having thermally formed therein a plurality of reagent receiving wells; adding a reagent to each of said reagent receiving wells; permitting each of said reagent receiving wells to incubate at a predetermined temperature for a predetermined time; and performing a biological analysis on each of said reagent receiving wells.

23 Claims, 10 Drawing Sheets

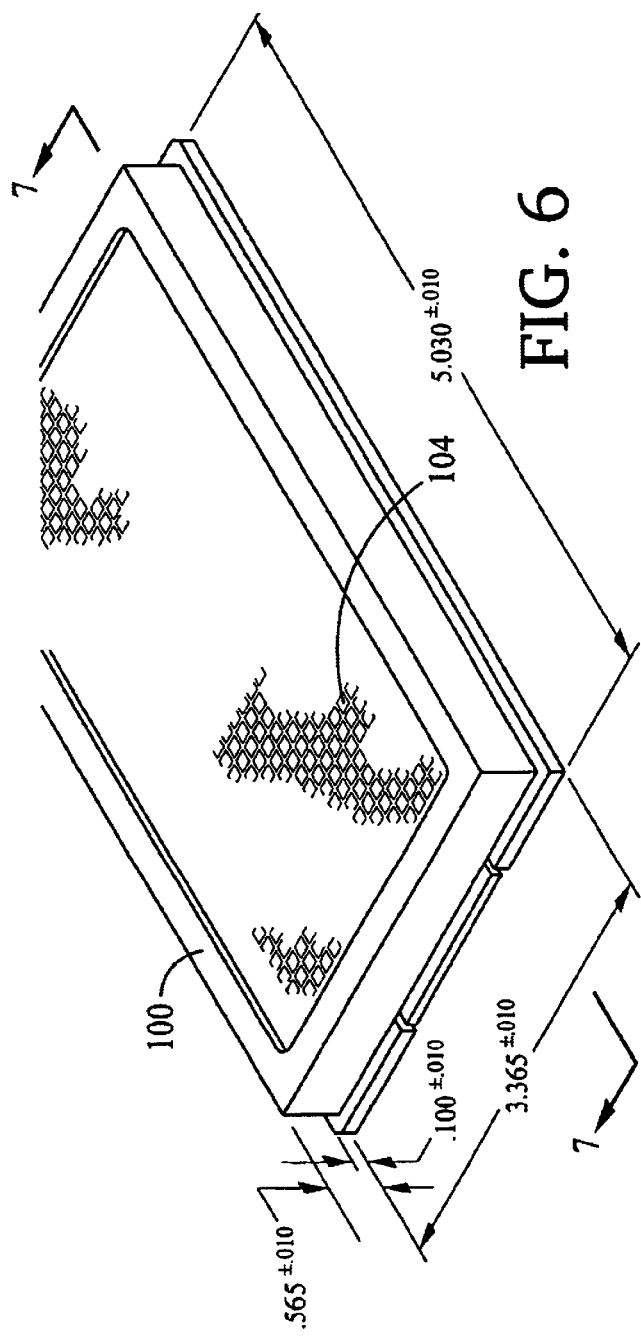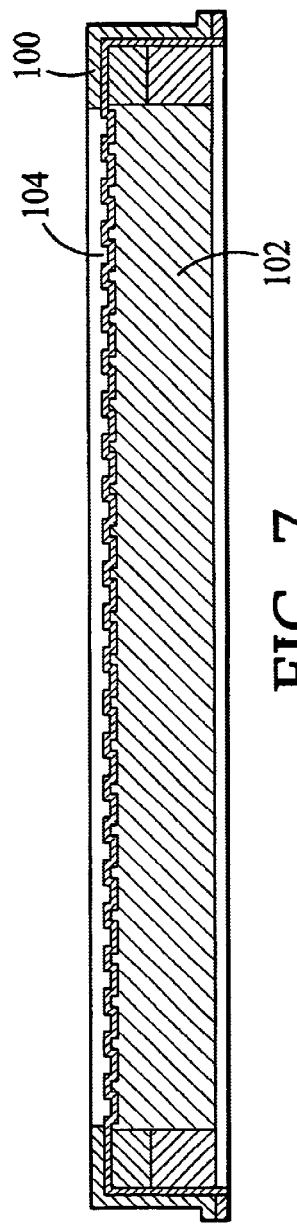
FIG. 6
FIG. 7

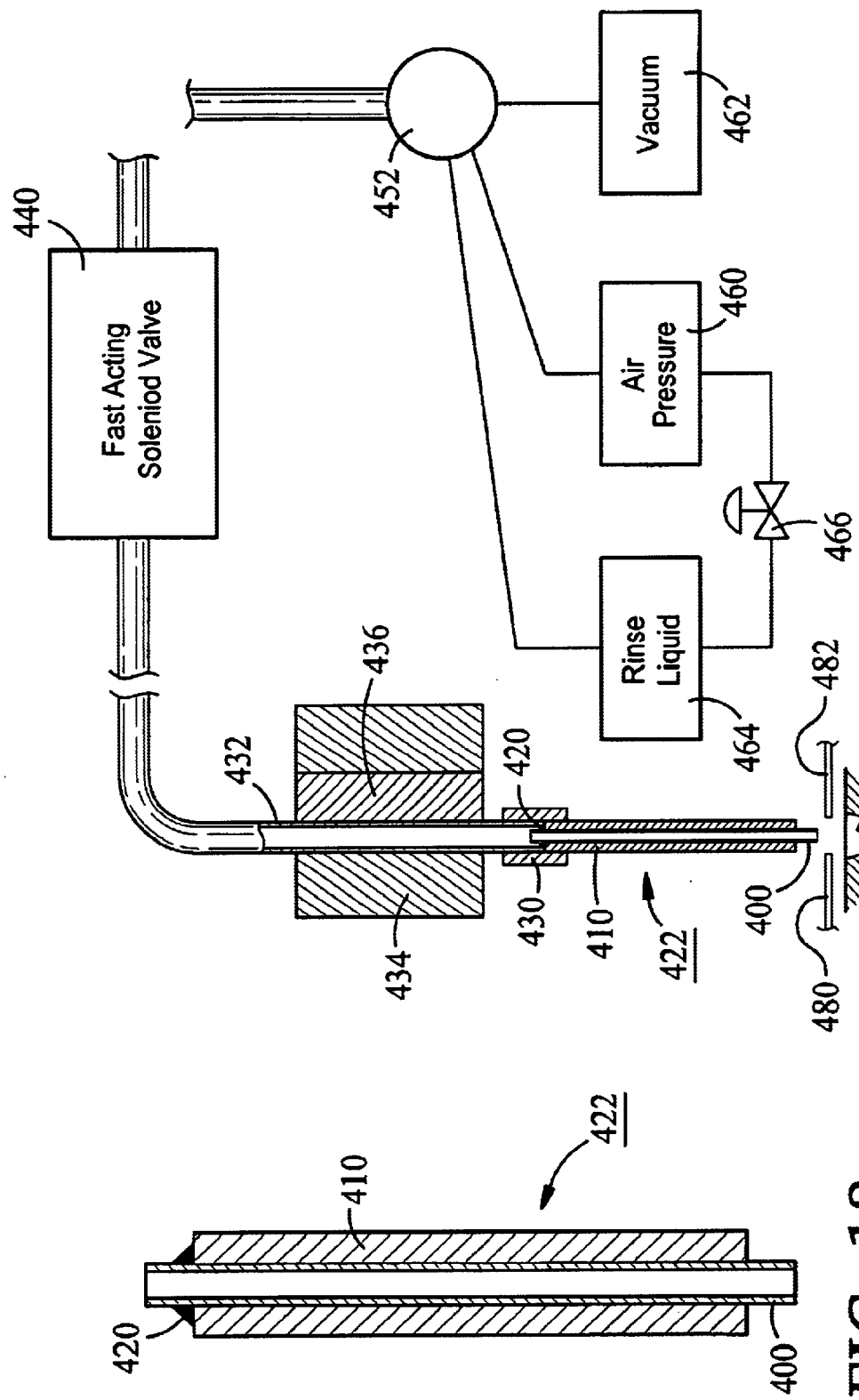

100
ULTRA HIGH THROUGHPUT BIOASSAY SCREENING SYSTEM

CROSS-REFERENCE TO RELATED APPLICATIONS

Benefit is claimed of the filing dates of U.S. Provisional Patent Applications No. 60/067,895, filed Dec. 8, 1997, and titled ULTRA HIGH THROUGHPUT BIOASSAY SCREENING SYSTEM AND METHOD; No. 60/073,329, filed Feb. 2, 1998, and titled ULTRA HIGH THROUGHPUT BIOASSAY SYSTEM AND METHOD; and No. 60/095,497, filed Aug. 6, 1998, and titled USE OF CONTINUOUS CARRIER TAPE FOR POLYMERASE CHAIN REACTIONS, the disclosures of which applications are incorporated by reference hereinto.

BACKGROUND OF THE INVENTION

1. Field of the Invention

The present invention relates to bioassay screening generally and, more particularly, but not by way of limitation, to a novel system for ultra high throughput bioassay screening.

2. Background Art

High Throughput Screening (HTS) has been in use for at least the past ten years to screen large numbers of potential chemical compounds that may have pharmaceutical efficacy or which may be precursors to pharmaceuticals. A given investigation may involve the screening of on the order of about 10,000 compounds per day. There are three basic areas of HTS: (1) handling the compound library, (2) lead discovery, and (3) lead optimization. Handling the compound library is an essential element of the other two. Lead discovery and lead optimization tend to overlap. The objective of lead discovery is to develop "hits" or what appear to be active compounds in specific areas. Lead optimization is a refinement of these "hits" so as to pass on qualified leads to medicinal chemistry for further development. Without this refinement, medicinal chemistry is swamped and the discovery of more "hits" is negated. The success of HTS has fostered the next step—a tenfold increase in throughput or Ultra High Throughput Screening (UHTS).

The primary objective of UHTS is to achieve more qualified lead compounds. In general terms, UHTS has been described as the ability to screen, in a given investigation, a library of 500,000 compounds against 50 therapeutic targets per year. This equates to 100,000 compounds screened per day. The economics of this number dictates some form of miniaturization to conserve the precious reagents consumed.

Since compound handling is the front end of both lead discovery and optimization, it must be considered first. The long term library storage is necessarily in solid or semi-solid form, for stability reasons. However, for use in screening, the library must be converted to a liquid phase. The most commonly accepted method of such conversion is to weigh out a small aliquot of a compound and solvate it with dimethyl sulfoxide (DMSO). Speed and convenience dictate weighing out typically 10 milligram quantities as the minimum amount. These are then brought into solution form, at, say, 10 millimolar concentration, yielding 5 to 10 ml of solution. This is then subdivided into smaller aliquots of 0.5 ml and stored frozen in sets of 96 deepwell tubes at −20 or −80 degrees Centigrade as an archive library.

Several areas of concern arise in going from the archive library to the usable form for the assay. First is the concentration—many assays are tested at $10^{-5}$ or $10^{-6}$ concentrations. The majority of assays cannot tolerate much more than 1% DMSO. Thus, a dilution from the archive library is required. However, some compounds, while soluble in 100% DMSO, are not soluble in lesser percentages. It is desirable to make the compound dilution in the final assay volume and not in a previous dilution step. Another concern is protecting the stability or validity of the archive compound. Freezing it lengthens its shelf life. But to access the compound, it must be thawed to remove an aliquot. Each time a freeze-thaw cycle occurs, there is the potential for moisture to degrade the compound. Thus, it is desirable to minimize these cycles. The real problem is how to transfer 100,000 discreet samples per. day from the archive library to the assay, keeping the above constraints in mind.

Since the libraries may contain upwards of 500,000 discreet compounds, a means is required to both aspirate multiple samples from the compound source and dispense multiple aliquots of nanoliter quantities into the assay destination. Since in the majority of biological assays, a concentration of more than 1% DMSO is toxic to the assay results and if an assay is to run at a 5 microliter volume, only 50 nanoliters of DMSO is allowed. The molarity of the compound solution in DMSO is adjusted so that 50 nanoliters of the compound solution also provides the desired concentration of compound to the assay.

Small individual piezo electric pumps have been utilized for the purpose of aspirating and dispensing these small quantities of liquids. The common method is for the piezo to squeeze an individual glass capillary to create a pressure wave to dispense liquid from within the capillary. Reversing the action will cause the capillary to aspirate liquid. The individual piezo pumps are costly to manufacturer, as are the electronics to drive them. In the pharmaceutical application, described above, it is necessary to rinse the flow passage with a suitable solvent, normally DMSO, to prevent sample-to-sample carry over. Due to the small displacement volume of the piezo pump device a considerable number of cycles or shots is required to pass a suitable quantity of wash fluid. The wash fluid must then be cleared from the pump so as not to dilute the next sample.

In such pharmaceutical research, due to the high numbers to be processed, the samples to be aspirated and dispensed are on very close centers, typically 4.5 mm, or 2.25 mm, or smaller. This places a severe limit on the size of the dispensing device. Due to the small quantities involved, more efficient liquid movement is obtained if the device causing fluid motion is close to the outlet orifice. Otherwise, the energy of the shockwave causing displacement is absorbed by the liquid in the pathway. This results in less velocity at the orifice. If the stream does not have sufficient velocity and kinetic energy at the orifice, it does not overcome the surface tension there and the form of delivery is as liquid drops; however, an ejected stream is desired especially when dispensing. This permits non-contact dispensing. The dispensing tip is not contaminated with other fluids—only the fluid being dispensed.

Accordingly, it is a principal object of the present invention to provide method and means for ultra high throughput screening.

It is a further object of the invention to provide such method and means that are economically implemented.

It is an additional object of the invention to provide such method and means that permit the economical simultaneous aspirating and dispenses of a large number of very small volumes of liquid.

It is another object of the invention to provide such method and means that provide for the compact storage of large numbers of chemical compounds.

It is yet a further object of the invention to provide liquid transfer method and means that employs a single piezoelectric crystal to simultaneously effect the aspiration or dispensing of a large number of liquid samples.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a method of performing biological assays, comprising: providing a longitudinally extending carrier tape having thermally formed therein a plurality of reagent receiving wells; adding a reagent to each of said reagent receiving wells; permitting each of said reagent receiving wells to incubate at a predetermined temperature for a predetermined time; and performing a biological analysis on each of said reagent receiving wells.

BRIEF DESCRIPTION OF THE DRAWING

Understanding of the present invention and the various aspects thereof will be facilitated by reference to the accompanying drawing figures, provided for purposes of illustration only and not intended to define the scope of the invention, on which:

FIG. 6 is an isometric view of a portion of a carrier tape inserted in a frame.

FIG. 7 is side elevational view, in cross-section, of the carrier tape and frame of FIG. 6.

FIG. 13 is a greatly enlarged, side elevational view, in cross-section, of a dispensing/aspirating needle constructed according to the present invention.

FIG. 14 is a side elevational view, partially in cross-section and partially schematic, of a dispensing/aspirating system according to the present invention.

DETAILED DESCRIPTION OF THE PREFERRED EMBODIMENTS

Figure 1:
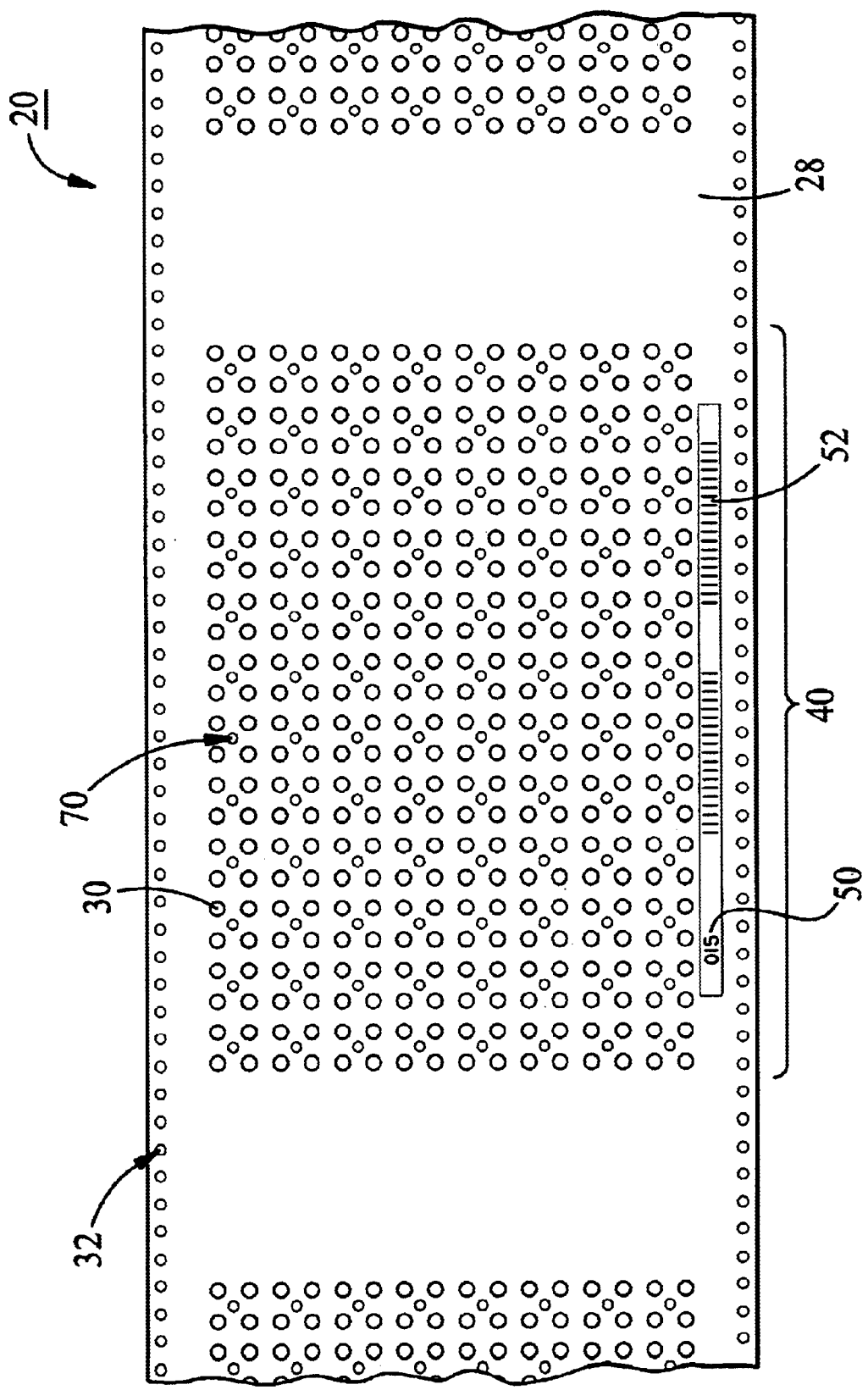
FIG. 1 is a top plan view of a carrier tape, having a plurality of bioassay wells formed therein, and constructed according to one aspect of the present invention.

Reference should now be made to the drawing figures on which similar or identical elements are given consistent identifying numerals throughout the various figures thereof, and on which parenthetical references to figure numbers direct the reader to the view(s) on which the element(s) being described is (are) best seen, although the element(s) may be seen on other figures also.

In one aspect of the invention, there is adapted a sprocket driven carrier tape, as a processing vehicle for biological assays. A similar type of tape is known in the electronics industry for transporting electrical components, such as is described in Electronic Industries Association documents EIA/IS_704 and others.

FIG. 1 illustrates a carrier tape, constructed according to the present invention, and generally indicated by the reference numeral 20. Carrier tape 20 is made from a heavy film, 15 to 20 mils thick, of a thermoformable resin. The type of resin used depends on the application. Polypropylene is a suitable candidate for those applications requiring chemical resistance. Polycarbonate film is a candidate for those applications involving growth, or supporting growth, of tissue culture and it may be supplied clear for colorimetric type assays. Polycarbonate or other materials may be supplied opaque, white, or black for fluorometric or luminescent assays.

Carrier tape 20 includes a substrate 28 which is processed to emboss therein a plurality of wells, as at 30, in specific patterns to hold liquid. A plurality of sprocket drive holes, as at 32, is provided along each edge. Sprocket drive holes 32 are precision punched to maintain a uniform spacing. This permits tractor driving carrier tape 20 for transport. Sprocket drive holes 32 also create a positional relationship to define any location on carrier tape 20 to provide recall to any selected well on the carrier tape.

Figure 2:
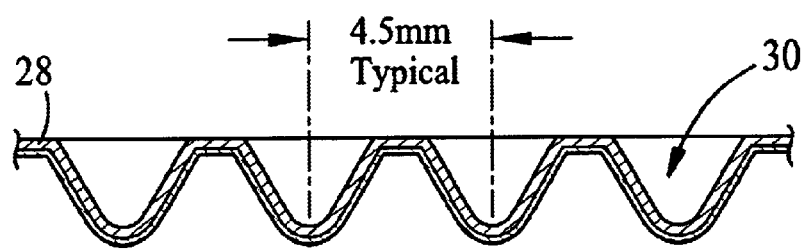
FIG. 2 is a fragmentary, side elevational view, in cross-section, of the carrier tape of FIG. 1.

The shape of wells 30 is a function of the application for carrier tape 20. For chemical compound storage, the walls of the wells may have a Vee shape with a rounded bottom, as shown on FIG. 2. For assays requiring an optical readout, the well may have a clear flat bottom. The required well shape is derived from the embossing tool.

The pattern of wells 30 is also a function of the application of carrier tape 20. The defacto standard for biological assays is the 96-well microplate (see Society for Biomolecular Screening 96-well plate standard). This is an 8×12 matrix of wells or receptacles on 9-mm center spacing. The need for higher numbers of assays and their miniaturization is fostering higher density formats. To be compatible with existing instrumentation and chemical libraries, these new formats are multiples of the 96-well format. The 384-well format is a 16×24 matrix on 4.5 mm centers. The 1536-well format is a 32×48 matrix on 2.25 mm centers. Any of these formats may be embossed in carrier tape 20 (FIG. 1). Carrier tape 20 has been embossed with a group 40 of wells 30. It will be understood that a plurality of additional such groupings will be provided axially along the length of the carrier tape.

Carrier tape 20, with its sprocket or tractor drive, provides a fast efficient way of transporting the reagent receiving patterns through the processing equipment. The inline processing provides considerable throughput advantages over handling the reagent patterns in individual injection molded plates. To provide pattern identification, each pattern on a roll of carrier tape is supplied with both a man readable identification number 50 and a machine readable identification number, in this case, a bar code 52, both printed on the bottom side of carrier tape 20 using ink jet or other suitable methods.

Another primary advantage of the use of carrier tape 20 is compact storage. One hundred thousand chemical compounds for UHTS, in 5 microliter aliquots, can be stored in a carrier tape roll 4 inches wide and 16 inches in diameter. This storage requires that the liquid contents of the wells be sealed with a leak tight seal. A further requirement, since later access to the liquid wells is required, is that the seal must be removable.

For chemical compound storage the carrier tape and seal material must be inert to both the chemical compound and the dimethyl sulfoxide (DMSO) used to solvate the compound. Polypropylene meets this requirement for the carrier tape. The seal layer may be a pressure sensitive adhesive or a heat seal. If pressure sensitive material is used it must be DMSO resistant. While the latter type of material is available, there is still the question of compatibility with the chemical compounds. For this reason a heat seal material is preferred.

Figure 3:
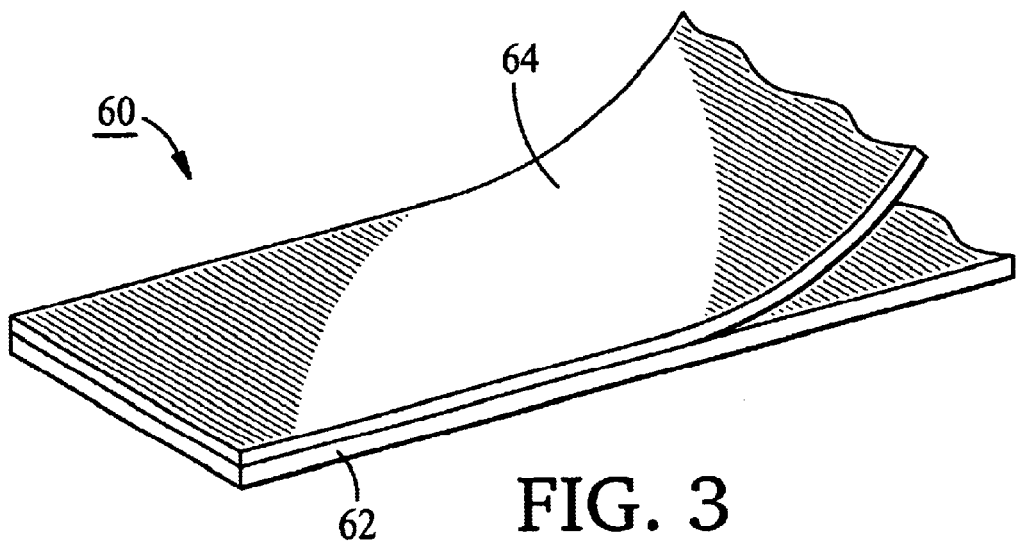
FIG. 3 is a fragmentary, isometric view, of a sealing layer for use over the carrier tape of FIG. 1.

FIG. 3 illustrates a heat seal layer, generally indicated by the reference numeral 60. Heat seal layer 60 is a two-part structure made by lamination or co-extrusion. A seal layer 62 is provided which has a low melting point, low tensile strength resin such as a modified low density polyethylene or an ethylene vinyl acetate copolymer. A top, or support, layer 64 is provided adjacent seal layer 62 and is a high temperature resin with good tensile strength properties. Polyester is commonly used. The high melting point of the polyester prevents it from sticking to the heat seal apparatus at the temperature required to bond the seal layer. The high tensile strength of the polyester supports the seal layer during seal and unseal operations. This type of bi-film is commonly used in lidding applications for the prepared food industry.

To obtain a valid leak proof heat seal requires that the carrier surface and the heat seal surface be held in intimate contact for the sealing period. The sealing period is a function of time and pressure. The carrier tape is indexed with an intermittent motion, such as that which is obtained with a walking beam drive.

Figure 4:
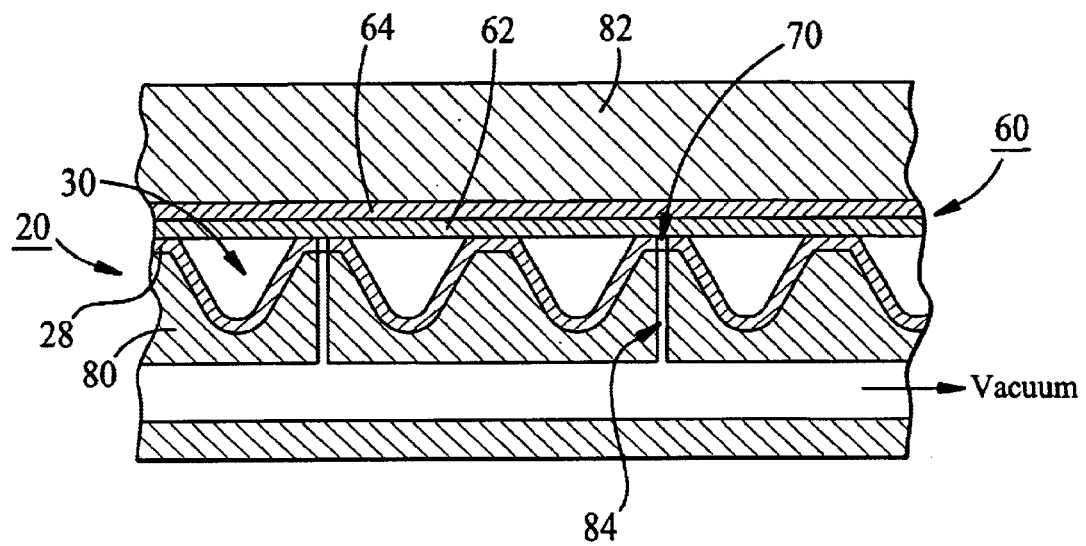
FIG. 4 is a fragmentary, side elevational view, in cross-section, of the mechanism by which the sealing layer of FIG. 3 placed on the carrier tape of FIG. 1.

As is illustrated on FIG. 4, at a sealing station, carrier tape 20 is held flat by means of a vacuum platen 80. Sealing layer 60 is fed from a roll (not shown) to a position between a heated sealing head 82 and carrier tape 20. Heated sealing head 82 brings sealing layer 60 and carrier tape 20 together under defined conditions of time, pressure, and temperature.

Air entrapped between the seal layer 62 and carrier tape 20 (FIG. 1) will inhibit the seal. To avoid this, carrier tape 20 is provided with a plurality of vent holes, as at 70, spaced between wells 30. This allows a plurality of passageways 84 formed in a vacuum platen 80 supporting carrier tape 20 to evacuate any entrapped air between the two films, effecting a leak proof seal. As shown on FIG. 4, passageways 84 and holes 70 are aligned.

Figure 5:
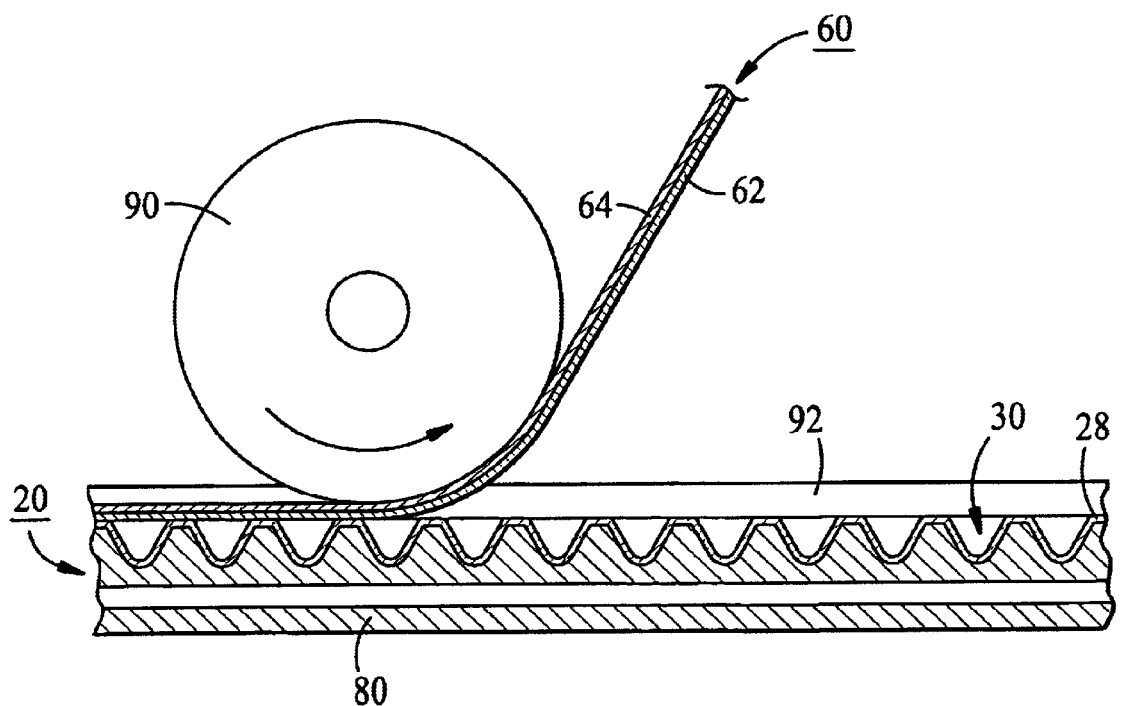
FIG. 5 is a fragmentary, side elevational view, in cross-section, of the mechanism by which the sealing layer of FIG. 3 is removed from the carrier tape of FIG. 1.

Removal of seal layer 60 may be achieved two ways. FIG. 5 illustrates an automated system in which sealed carrier tape 20 is passed under a heated roller 90. Polyester top layer 64 prevents sticking to roller. Roller temperature and contact time are controlled by the machine parameters. Seal layer 62 is softened and the strength of polyester layer 64 is used to separate the seal. A take up winder (not shown) on which seal layer 62 is wound, provides the tensile force necessary to break the seal. Carrier tape 20 is held down by edge guides 92 that are outside of the sealed pattern.

Some biological materials may be degraded by the heat from the unsealing. To eliminate that possibility, vacuum platen 80 supporting carrier tape 20 at the unsealing station may be refrigerated.

There are two basic applications of carrier tape 20—use with automated systems and use with manual systems. This is particularly true where carrier tape 20 is used for chemical compound storage for pharmaceutical screening. Use of carrier tape 20 for that concept provides an exceptional method for the central compound library to distribute aliquots of compounds to outlying investigators. Each pattern 40 of compounds on the carrier tape has its own identification number imprinted on it. It may be cut from the carrier tape and handled as a separate entity. This creates the need of different solutions to handle individual patterns.

As is illustrated on FIGS. 6 and 7, with manual systems, the primary usage of the present invention is the introduction of compounds into assays performed in microplates. This is accomplished with a special frame of two-part construction, the frame having an outer shell 100 (FIG. 6) with an internal opening which meets the external footprint of the standard for a 96-well microplate. Thus, it will fit instrumentation designed for such microplates. An inner retainer 102 (FIG. 7) snaps into the outer frame to support a section of carrier tape pattern 104. Inner retainer 102 holds flat carrier tape 104 to facilitate aspirating liquid from the wells with a multiple tip pipettor consisting of 384 or 96 tips.

Special requirements are required to unseal the individual section of carrier tape pattern 104. It is desirable to unseal the pattern 104 after it is retained and used in outer shell frame 100. The edge of the seal on carrier tape 104 is clamped between outer shell frame 100 and inner retainer 102. For manual use, the seal is die cut with a steel rule die (not shown). It is die cut within the confines of the outer frame. Thus, a user can catch an edge of and strip carrier tape section 104 from the well area.

Most chemical compounds are solvated in dimethyl sulfoxide (DMSO). DMSO freezes at +4° C. (+40° F.). To minimize compounds being removed with the seal, inner retainer 102 is chilled prior to assembly of carrier tape section 104 in the frame. This is sufficient to solidify the DMSO to assure that the compounds remain in the wells and are not removed with the seal.

In normal operation, rolls of carrier tape 20 (FIG. 1) filled with chemical compound aliquots would be stored frozen at −20° C. or even −80° C. The compact nature of this storage system allows a very large number of chemical compounds to be stored in one freezer. Once removed from the freezer, the carrier tape system has a minimum of latent heat storage, both in the tape itself and in the small volume of liquid it contains. This has the advantage of a quick defrost prior to use, whereas microplate storage systems may require the better part of a day to defrost.

The disadvantage of the quick defrost is that the time in handling the roll may exceed the defrost time. The handling of the sealed roll may cause some of the well contents to move away from the bottom of the well. This is compensated for, by spinning the roll on its unwind stand prior to use in the application. Centrifugal force will move the liquid to the well bottom. Surface tension will retain it there during the gentle handling of the unwind stand during processing.

Biological assays and protocols utilizing polymerase chain reaction (PCR) require multiple cycles of different temperatures, usually three. These protocols are currently processed in microplates, 96-well or 384-well. A microplate is placed in its own thermal cycling instrument. Because of the latent heat capacity of the microplate, the majority of processing time is due to changing the temperature of the microplate—not the reagent it contains. The carrier tape system of the present invention will greatly improve the speed of processing PCR, a vital protocol in the Human Genome Project and other genomic studies.

Figure 8:
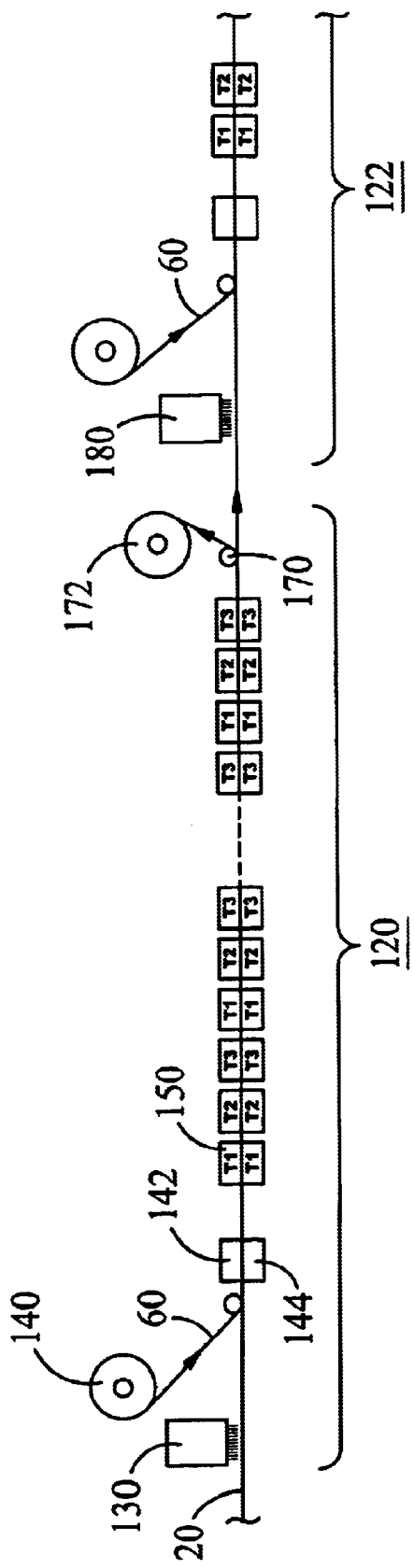
FIG. 8 is a schematic view of a polymerase chain reaction (PCR) processing line employing the present invention.

The small latent heat capacity of the carrier tape and its speed of precise movement open a new vista for PCR. Instead of cycling temperature about a fixed microplate, the carrier tape can be quickly transported from one temperature station to the next as illustrated on FIG. 8 which shows a PCR processing line employing the present invention. A first reagent processor, generally indicated by the reference numeral 120, is provided and a second reagent processor, generally indicated by the reference numeral 122 may also be provided. Similar additional reagent processors can be provided as needed. Suitable motive means indexes carrier tape 20 to the right on FIG. 8. A first pipettor 130, which may be assumed to be a 384-well pipettor, adds a first-set of reagents to wells 30 (FIG. 1) on carrier tape 20. Sealing film 60 is fed from a supply roll 140 to a sealing station comprising a heat seal bar 142 which provides closure by applying pressure and heat to seal layer 60 and carrier tape 20 and a heat seal anvil 144 backs up the seal bar. Heat seal anvil also applies vacuum to hold carrier tape 20 flat similar to vacuum platen 80 (FIG. 4). The application of vacuum will also evacuate any entrapped air between seal layer 60 and the surface of carrier tape 20.

Carrier tape 20 then indexes through a series of temperature control stations, as at 150. The time at each station 150 is a function of the index time. In many applications, a common temperature dwell time is satisfactory. In those protocols where a common time is not acceptable, an individual temperature station would be opened at its selected time interval.

Figure 9:
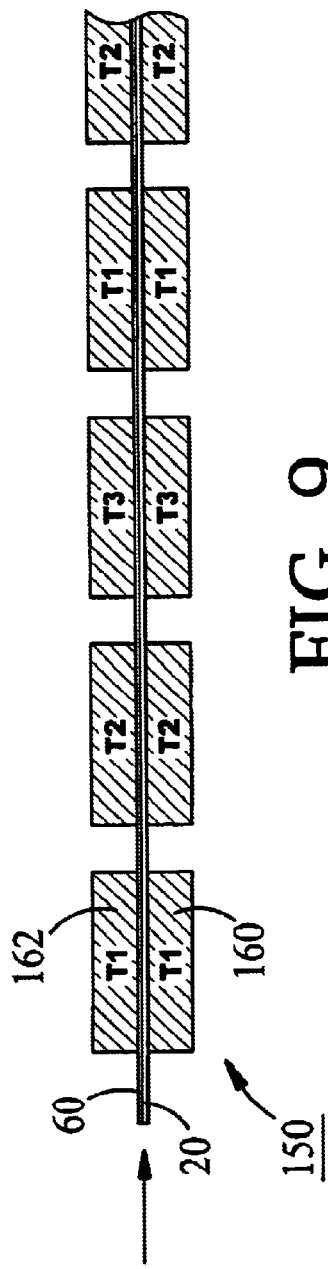
FIG. 9 is a schematic detail of a portion of FIG. 8.

As illustrated more clearly on FIG. 9, in addition to having a heated bottom portion 160, each temperature control station has a heated lid 162. This provides quick uniform temperature to the contents of the wells.

Referring back to FIG. 8 after passing through the required temperature cycles, seal layer 60 may be removed for access to the contents of the wells. As described before, a heated roll 170 warms the seal area. A seal winder 172 provides tension on the seal layer 60, to remove it from carrier tape 20. With the wells open, the contents may be removed or additional reagents added. In the latter case, a second pipettor 180 adds the second set of reagents and the entire protocol repeated on second reagent processor 122.

Each temperature station 150 is maintained at a fixed, easily regulated temperature. As carrier tape 20 is indexed to each station 150, the temperature of the small volume of reagents within the wells will quickly reach the equilibrium temperature of the specific station.

Due to the small volume of reagents in the wells and the high temperature of PCR (typically 90° C.), evaporation is a real concern. Another concern is contamination, well to well, due to the high amplification of PCR. The ability to seal each well with a leakproof seal, as described before, provides an ideal solution for both problems. Access to the wells is required at the end of the PCR. The ability to unseal the carrier tape automatically meets that requirement.

Many biological assays require an incubation period following the addition of reagents. The incubation period may have environmental demands (i.e., elevated temperature typically 37° C., high humidity to minimize evaporation from open wells, or a $CO_2$ environment for cell viability). This may be easily provided on a carrier tape system by cutting the carrier tape into convenient length (i.e. 4 feet long).

Figure 10:
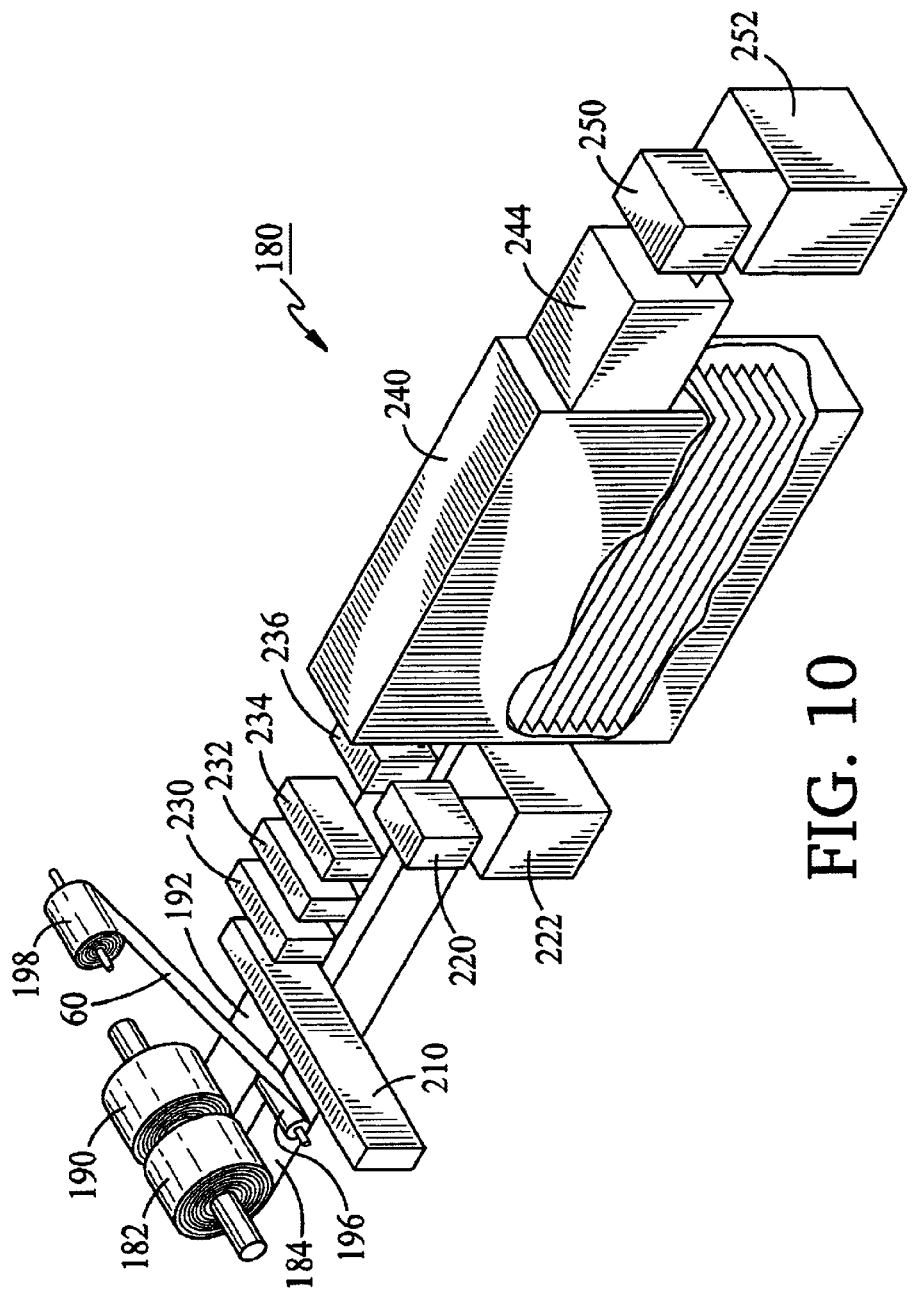
FIG. 10 is a schematic, isometric view of a PCR processing line including an incubator.

A system providing for incubation prior to fluorescence reading is illustrated on FIG. 10 where the system is indicated generally by the reference numeral 180. System 180 includes a first supply roll 182 of sealed carrier tape 184, similar to carrier tape 20 (FIG. 1), containing a large number of chemical compounds, and a second supply roll 190 of unsealed assay carrier tape 192, also similar to carrier tape 20, however, having empty wells. As compound tape 184 is unrolled, it passes under a heated roller 196 which removes sealing layer 60 which is wound on roller 198 in the manner described above with reference to FIG. 8.

Tapes 184 and 192 are indexed under a compound transfer manifold 210 which transfers chemical compounds from the wells on compound carrier tape 184 to the wells on assay carrier tape 192. Compound carrier tape 184 can then be discarded as by means of a tape cutter 220 and a waste container 222.

After the transfer of chemical compounds by compound transfer manifold 210, assay carrier tape 192 is indexed under a first reagent manifold 230 for introduction of reagents into the wells on the tape, then, if required, under a second reagent manifold 232 for the introduction of additional reagents, and then, if required, one or more additional reagent manifolds. Assay carrier tape 192 is then indexed under a standards and controls manifold 234 and then under a tape cutter 236 where the tape is cut into, for example, 4-foot lengths. The cut lengths of assay carrier tape 192 are then transported, using a tractor drive, into an incubator 240. Incubator 240 can be very compact, with a unit 6 inches wide by 24 inches deep by 4 feet long accommodating 100,000 wells of the type described above with reference to FIGS. 1 and 2. After the required incubation period, each strip moves to the next processing station, in this case a fluorescence reader 244 which may read, for example, fluorescence intensity, fluorescence polarization, luminescence, or time resolved fluorescence. After reading, each section of tape 192 can then be disposed of by means of a tape cutter 250 and a waste container 252.

Figure 11:
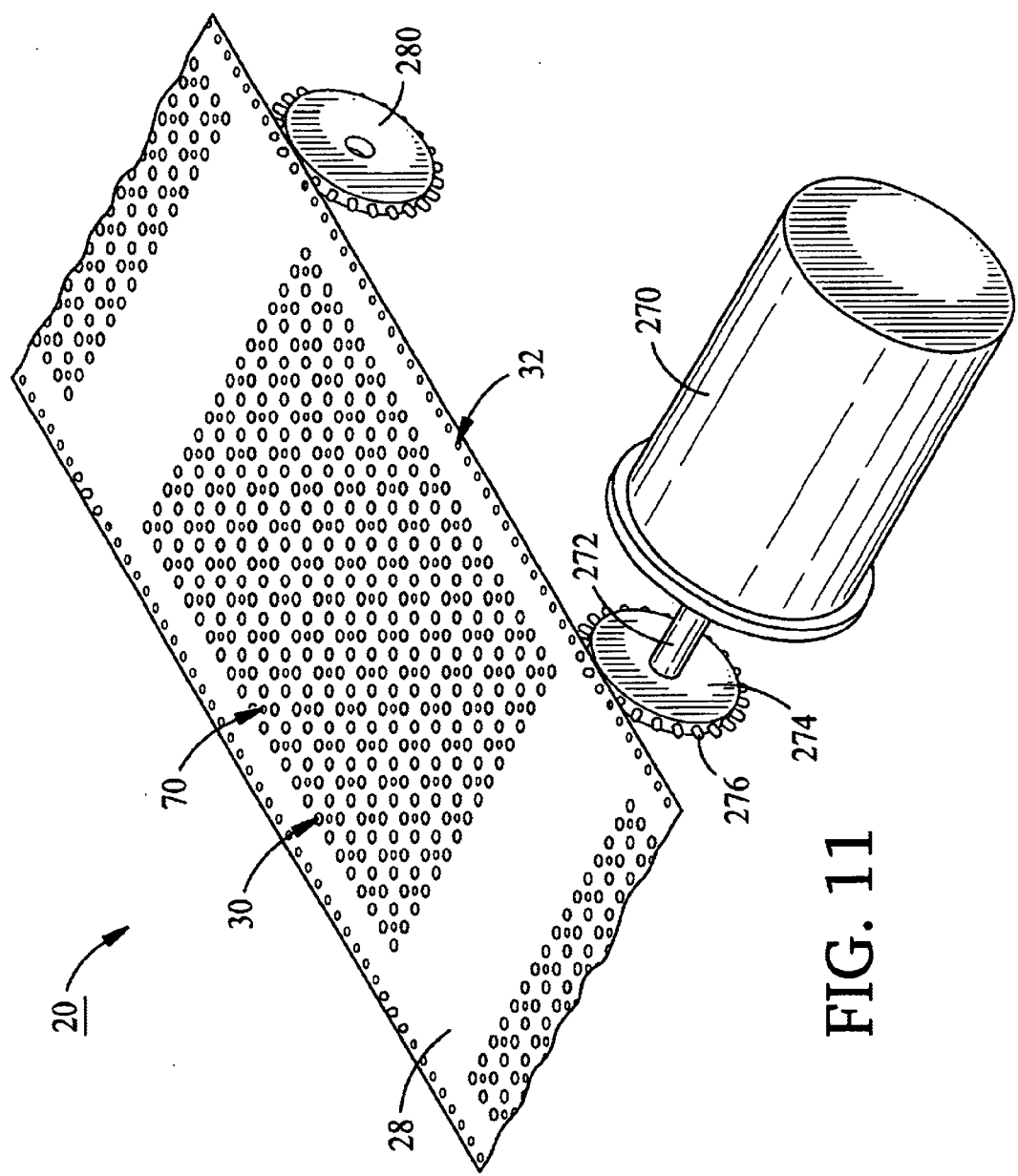
FIG. 11 is a fragmentary, isometric view of a tractor drive for moving the carrier tape of FIG. 1.

FIG. 11 illustrates the major components of a tractor drive for moving carrier tape 20. A motor 270, which may be a stepper motor, has a rotatable shaft 272 to which is affixed a sprocket wheel 274. Sprocket wheel has a plurality of sprockets, as at 276, extending outwardly from the outer periphery thereof, the sprockets engaging sprocket holes 32 in carrier tape 20. As motor 270 rotates sprocket wheel 274, carrier tape 20 is driven in one direction or the other. One or more sprocket idler wheels 280 are provided to support and guide carrier tape 20. The extent of travel of carrier tape 20 may be determined by an encoder (not shown) associated with one of the rotary components of the tractor drive, by counting the number of sprocket holes 32 passing a given point by optical or other means, and/or by identifying indicia, such as bar code 52 (FIG. 1), on the carrier tape.

Figure 12:
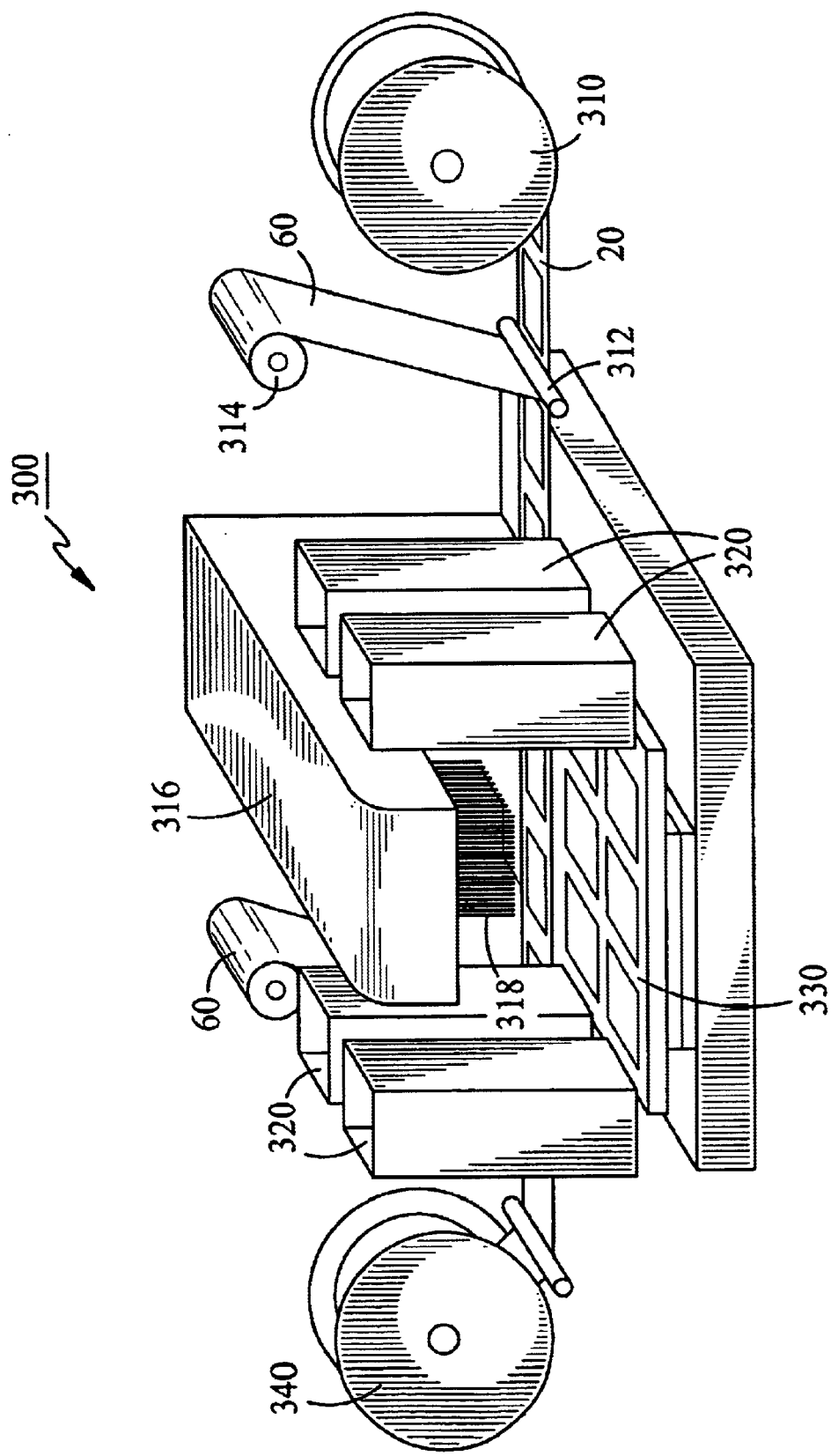
FIG. 12 is a schematic, isometric view of a compound transfer station employing the present invention.

FIG. 12 illustrates a compound transfer system employing the present invention, the system being generally indicated by the reference numeral 300. Here, sealed carrier tape 20 containing a large number of chemical compounds is unrolled from a supply roll 310, sealing layer 60 is removed from the carrier tape by means of a heated roller 312 and a winder roller 314, and the carrier tape is indexed under a 384-well pipettor 316 with a transverse moving head having 384 needles depending therefrom. Such a pipettor may be a Quadra384 Pipettor as furnished by Tomtec, Inc., of Hamden, Conn. Included in system 300 are two pairs of dual reversible stackers 320 which, depending on programming, supply standard 384-well microplates to an six-position X-Y shuttle 330 or accept the microplates from the shuttle. The open wells on carrier tape 20 can be accessed by pipettor 316. Using "pipeline" pipetting, pipettor 316 aspirates the various reagents in the assay using an air gap for separating the reagents. The standards and controls are aspirated from special reservoirs (not shown) to match the user's format. The ability of pipettor 316 to aspirate 0.5 microliter quantities permits aspirating compounds from carrier tape 20 in 100% DMSO, while maintaining a 1% DMSO concentration in the 50 microliter assay volume. In addition, to speed processing, pipeline pipetting uses high volume reagents (i.e., buffer) to wash out the small volume of compound from the pipettor tips, thereby maintaining precision in the assay. After dispensing the tip volume in an assay microplate, the plate is restacked in one of stackers 320, the pipettor tips are washed in an ultrasonic tip wash station (not shown), and the next microplate is infed from a stacker and the cycle is repeated.

After use, carrier tape 20 can be discarded or, if the chemical compounds thereon are to be saved for future use, a sealing layer 60 may be applied and the carrier tape wound on storage roll 340.

Another aspect of the present invention is to provide means to both aspirate and dispense multiple aliquots of nanoliter quantities. The unique principle of this invention is to have one piezo crystal exert sufficient force on multiple tubes to deform them to displace the desired volume. The amount of force, and thus displacement, is controlled by the electronics driving the piezo crystal. The dispensing tubes being deformed remain within their elastic limit. When the piezo crystal retracts, the cross section of each dispensing tube returns to its original cross sectional area, thereby creating the aspirate/dispense action.

The nanoliter volumes require a very small diameter orifice. This generates the back pressure against the shockwave that creates the stream velocity through the orifice. Not only must the inside diameter be small, but also the wall thickness must be thin, requiring a small outside diameter. A heavy wall section creates additional surface area at the orifice, increasing the surface tension forces. The thin walled small orifice tube results in a fragile dispensing tube. This presents both reliability and manufacturing problems.

The present invention uses a small dispensing needle 400, as illustrated on FIG. 13. Typically, the inside diameter of needle 400 is 0.003 inch with an outside diameter of 0.012 inches. This provides a 0.0045-inch wall section. Dispensing needle 400 is fitted inside of a supporting needle 410 having an inside diameter of 0.016 inch allowing a slip fit of the outside diameter of the dispensing needle. Needles 400 and 410 are bonded at the tops thereof with a suitable material, such as UV cured epoxy or polyurethane adhesive, to form a liquid-tight seal 420. Needles 400 and 410 together form a needle assembly, generally indicated by the reference numeral 422.

Figure 15:
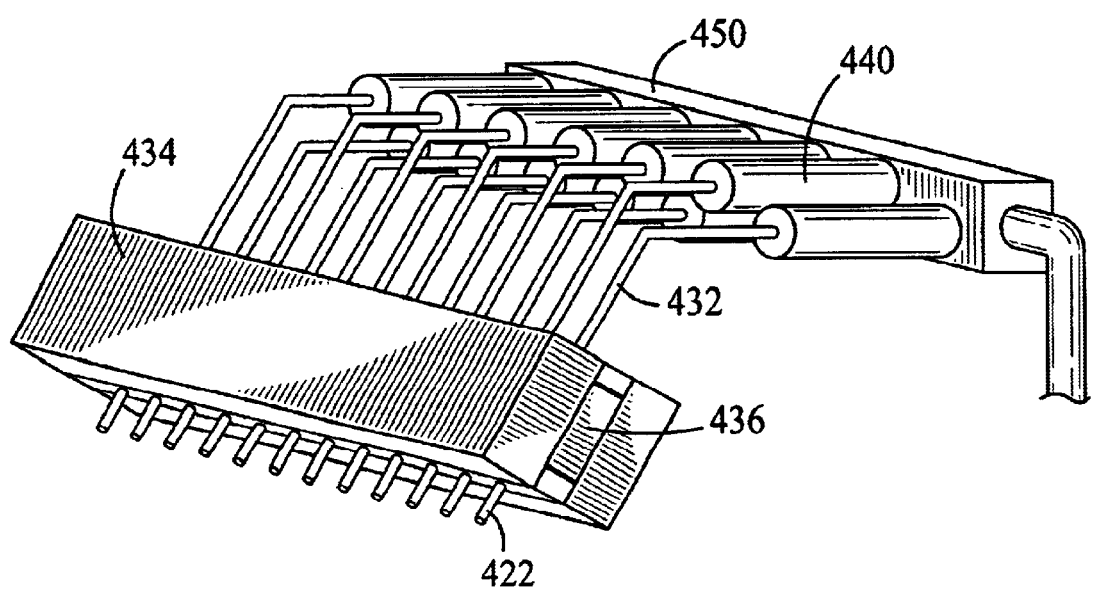
FIG. 15 is an enlarged, fragmentary, isometric view of a dispensing/aspirating system according to the present invention.

As shown on FIG. 14, each needle assembly 422 is connected with a sleeve 430 of suitable material to a pump tube 432. Pump tube 432 is of a suitable cross section and length for the designed delivery volume. Pump tube 432 is retained between a rigid back up plate, or anvil, 434 and a piezo crystal assembly 436. The available movement of piezo crystal assembly 436 is also a variable in this equation. As is shown on FIG. 15, multiple pump tube 432 and their associated delivery needle assemblies 422 may be operated by one piezo crystal assembly 436. Piezo crystal assembly 436 is contained within the same anvil assembly 434 such that an increase in size of the piezo crystal causes a decrease in size of pump tubes 432. This provides the necessary pumping action, by displacement. Referring principally to FIG. 14, the other end of pump tube 432 is connected to a small fast acting solenoid valve 440 such as used in ink jet printing. During the dispense part of the cycle solenoid valve 440 is closed, blocking flow from pump tube 432 at that end. Only the orifice end of needle 400 remains open to the atmosphere.

Referring again to FIG. 15, an individual solenoid valve 440 is connected to each pump tube 432, although only one piezo crystal assembly 436 may be used to squeeze multiple pump tubes. Each solenoid valve 440 is connected through a manifold 450 to a common 3-way valve 452 (FIG. 14). Three-way valve 452 selectively connects all solenoid valves 440 to a source of air pressure 460, a source of vacuum 462, or a source of rinse liquid 464. Rinse liquid reservoir 464 is a closed container that is pressurized by a regulated air pressure through a valve 466.

The sequence of operation is as follows. Piezo crystal assembly 436 is energized to an initial holding or home position. This position compensates for any variation in the outside diameter of the multiple pump tubes 432. From this home position, all pump tubes 432 will be compressed the same dimension. The multiple delivery needles 400 are then dipped into the various wells, or reservoirs 470 (FIG. 14) containing the liquid to be aspirated. Three-way valve 452 connects all solenoid valves 440 to vacuum source 462. With the tips of delivery needles 400 submerged, solenoid valves 440 open and reclose quickly and are open long enough to allow the vacuum to aspirate liquids up through the area of piezo crystal assembly 436 and into pump tubes 432. Solenoid valve 440 closes before the liquid can reach the interior components of the solenoid valve. The length of pump tube 432 is sized to allow for variations in flow of the different liquids. The minimum flow for each liquid flow path is that the liquid line must pass the end of the pump tubes 432 and not reach the inlet of solenoid valve 440.

With pump tubes 432 filled, delivery needles 400 are moved to the dispense position. Piezo crystal assembly 436 is energized to its set value, causing a uniform and quick constriction of all pump tubes 432. This constriction displaces the fluid within pump tubes 432, causing delivery at the orifice of needles 400.

The next position of delivery needles 400 depends on the system function that is desired. The remaining contents of pump tube/needle assembly 432/400 may be reclaimed back into the origin or they may be deposited in a waste container. This is a similar function, but with the waste disposal, it is combined with the rinse function. The reclaim function is described, as follows. Three-way valve 452 switches to apply air pressure to all solenoid valves 440. With delivery needles 400 in the reclaim position, solenoid valves 440 open. Air pressure blows the remaining contents of the pump tube/delivery needle assembly 432/400 back into the origin reservoir.

Solenoid valves 440 close and needle assemblies are then moved to the waste/rinse position. Three-way valve 452 switches to the rinse liquid supply 464. Solenoid valves 440 open, admitting wash liquid to delivery needles 400, rinsing them to waste. At the completion of the wash cycles, solenoid valves 440 close. Three-way valve 452 then switches to pressure. Solenoid valves 440 open, blowing the remaining wash fluid contents in the system to waste. With the flow passages clear, the entire cycle repeats for the next aspirate/dispense cycle.

The amount of compression on pump tubes 432 is directly related to the volume dispensed from the outlet orifices of needles 400. In turn, the compression imparted by the piezo crystal assembly 436 is a function of its electrical excitation. This relationship is used to control the volume of liquid aspirated or dispensed on each cycle.

A closed loop monitoring system may be provided by locating a fiber optic transmitting and receiving pair 480/482 (FIG. 14), looking across each dispensing orifice of a needle 400. Fiber optic pair is 480/482 is connected to a light emitting diode and a phototransistor (not shown). A base line of conduction in the phototransistor is obtained when there is no flow from the orifice. When there is flow from the orifice, the conduction of the phototransistor is varied during the period of flow. This signal may be amplified and used to monitor or control the excitation to piezo crystal assembly 436. Only one piezo crystal assembly 436 is used to operate multiple orifices. Thus, the phototransistor signals would be averaged to provide feedback control to the piezo excitation. The individual orifice signals would be used to monitor flow or no flow from each orifice on each dispense cycle. If an orifice becomes clogged or otherwise ceases to function properly an error signal may be generated and corrective action can be taken. If individual piezo crystals are used on each pump tube then the photo transistor pair can have full feedback control on each delivery orifice.

In the embodiments of the present invention described above, it will be recognized that individual elements and/or features thereof are not necessarily limited to a particular embodiment but, where applicable, are interchangeable and can be used in any selected embodiment even though such may not be specifically shown.

Terms such as "upper", "lower", "inner", "outer", "inwardly", "outwardly", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A method of chemical compound storage, comprising:
   (a) providing a longitudinally extending carrier tape having therein two or more matrices of thermoformed chemical receiving wells, each of said two or more matrices being separated longitudinally from an adjacent one of said two or more matrices by a space greater in dimension than a space separating adjacent ones of said chemical receiving wells;
   (b) simultaneously adding to each of said chemical receiving wells in one of said two or more matrices a chemical compound; and
   (c) then, simultaneously adhering a sealing material around each of said chemical receiving wells in one of said two or more matrices to retain said chemical compounds therein and to minimize evaporation from said chemical receiving wells.

2. A method of chemical compound storage, as defined in claim 1, further comprising: attaching said sealing material to said carrier tape around each of said chemical receiving wells using a pressure sensitive adhesive.

3. A method of chemical compound storage, as defined in claim 2, further comprising: forming said carrier tape into a compact roll for storage, said roll having about 100,000 aliquots and dimensions of about 16 inches in diameter by four inches wide.

4. A method of chemical compound storage, as defined in claim 1, further comprising: providing said carrier tape of a thermoformable material having a thickness on the order of from about 15 mils to about 20 mils.

5. A method of chemical compound storage, as defined in claim 1, further comprising: providing said carrier tape formed of polypropylene to provide solvent resistance.

6. A method of chemical compound storage, as defined in claim 1, further comprising: providing said carrier tape formed of clear polycarbonate or polystyrene to facilitate optical reading of contents within said chemical receiving wells.

7. A method of chemical compound storage, as defined in claim 1, further comprising: providing said chemical receiving wells in said two or more matrices selected from the group consisting of 8×12 wells with a spacing of 9 mm between centers, 16×24 wells with a spacing of 4.5 mm between centers, and 32×48 wells with a spacing of 2.25 mm between centers.

8. A method of chemical compound storage, as defined in claim 7, further comprising: providing each of said repetitive matrices with a unique identifier.

9. A method of chemical compound storage, as defined in claim 2, further comprising: removing said sealing material after adhesion, using said pressure sensitive adhesive, to said carrier tape by pulling said sealing material from said carrier tape without the use of a knife structure.

10. A method of chemical compound storage, as defined in claim 1, further comprising: providing said sealing material removably heat sealed to said carrier tape to permit removal of said sealing material after being adhered to said carrier tape by pulling said sealing material from said carrier tape without the use of a knife structure.

11. A method of chemical compound storage, as defined in claim 10, further comprising providing said seal material as a two layer material having:
   (a) a lower, seal layer of a low melting point material inert to the contents of said chemical receiving wells; and
   (b) an upper high melting point layer having a higher tensile strength than said seal layer and being joined to said seal layer, to assist in removing said sealing material from said carrier tape.

12. A method of chemical compound storage, as defined in claim 11, further comprising: providing said lower seal layer formed of a material selected from the group consisting of modified low density polyethylene and ethyl vinyl acetate.

13. A method of chemical compound storage, as defined in claim 11, further comprising: providing said upper layer formed from polyester.

14. A method of chemical compound storage, as defined in claim 2, further comprising: removing said sealing material from said carrier tape by using a heated roll to warm said sealing material for removal.

15. A method of chemical compound storage, as defined in claim 2, further comprising:

(a) perforating said carrier tape with holes between said chemical receiving wells, said holes being disposed near upper edges of said chemical receiving wells; and (b) evacuating-space between said seal material and said carrier tape at time of sealing through said holes to assure an intimate leak tight seal is achieved between said seal material and said carrier tape.

16. A method of chemical compound storage, as defined in claim 2, further comprising: die cutting said sealing material around one of said two or more matrices of said chemical receiving wells to allow manual removal of said sealing material from said pattern of said chemical receiving wells.

17. A method of chemical compound storage, as defined in claim 3, further comprising: spinning said roll to force contents of said chemical receiving wells to bottoms of said chemical receiving wells by centrifugal force.

18. A method of chemical compound storage, as defined in claim 1, further comprising: severing individual said two or more matrices of said chemical receiving wells from said carrier tape so that said individual said two or more matrices can be used independently.

19. A device for chemical compound storage, comprising: a longitudinally extending carrier tape having therein a plurality of thermoformed chemical receiving wells, said chemical wells being disposed in two or more matrices on said carrier tape and a liquid tight sealing material adhered around each of said thermoformed chemical receiving wells to retain said chemical compounds therein and to minimize evaporation of said chemical compounds.

20. A device for chemical compound storage, as defined in claim 19, wherein said liquid tight sealing material is adhered to said carrier tape around each of said chemical receiving wells using a pressure sensitive adhesive.

21. A device for chemical compound storage, as defined in claim 20, wherein: said carrier tape is formable into a compact roll for storage, said roll having about 100,000 aliquots and dimensions of about 16 inches in diameter by four inches wide.

22. A method of chemical compound storage, as defined in claim 1, further comprising: indexing said two or more matrices of said thermoformed chemical receiving wells using a tractor drive.

23. A device for chemical compound storage, as defined in claim 19, further comprising: adhering said liquid tight sealing material around said chemical receiving wells on said carrier tape using a heat sealed material.

* * * * *

UNITED STATES PATENT AND TRADEMARK OFFICE
CERTIFICATE OF CORRECTION

PATENT NO. : 6,878,345 B1
DATED : April 12, 2005
INVENTOR(S) : Thomas W. Astle

It is certified that error appears in the above-identified patent and that said Letters Patent is hereby corrected as shown below:

Column 11,
Line 12, is corrected by cancelling "scaling" and inserting therefore -- sealing --.

Signed and Sealed this

Seventh Day of June, 2005

JON W. DUDAS
*Director of the United States Patent and Trademark Office*